(12) United States Patent
Johnston et al.

(10) Patent No.: US 7,032,593 B2
(45) Date of Patent: Apr. 25, 2006

(54) INHALATION DEVICE AND METHOD

(75) Inventors: Lloyd P. Johnston, Belmont, MA (US);
Kevin Stapleton, Boston, MA (US)

(73) Assignee: Advanced Inhalation Research, Inc.,
Cambridge, MA (US)

( * ) Notice: Subject to any disclaimer, the term of this patent is extended or adjusted under 35 U.S.C. 154(b) by 0 days.

(21) Appl. No.: 10/123,319

(22) Filed: Apr. 17, 2002

(65) Prior Publication Data

US 2002/0108611 A1 Aug. 15, 2002

Related U.S. Application Data

(62) Division of application No. 09/637,940, filed on Aug. 14, 2000, now abandoned.

(51) Int. Cl.
*A61M 15/00* (2006.01)

(52) U.S. Cl. .............................. 128/203.15; 128/203.12

(58) Field of Classification Search ........... 128/200.14, 128/200.23, 203.15, 203.12, 203.23, 203.21
See application file for complete search history.

(56) References Cited

U.S. PATENT DOCUMENTS

| | | | |
|---|---|---|---|
| 3,635,219 A | 1/1972 | Altounyan et al. | |
| 3,669,113 A | 6/1972 | Altounyan et al. | |
| 3,795,244 A | 3/1974 | Lax et al. | |
| 3,837,341 A | 9/1974 | Bell | |
| 3,888,253 A | 6/1975 | Watt et al. | |
| 3,906,950 A | 9/1975 | Cocozza | |
| 4,013,075 A | 3/1977 | Cocozza | |
| 4,069,819 A | 1/1978 | Valentini et al. | |
| 4,105,027 A | 8/1978 | Lundquist | |
| 4,192,309 A | 3/1980 | Poulsen | |
| 4,240,418 A | 12/1980 | Rosskamp et al. | |
| 4,338,931 A | 7/1982 | Cavazza | |
| 4,841,964 A | 6/1989 | Hurka et al. | |
| 4,846,168 A * | 7/1989 | Abiko et al. | 128/203.15 |
| 4,860,740 A | 8/1989 | Kirk et al. | |
| 4,889,114 A | 12/1989 | Kladders | |
| 4,995,385 A | 2/1991 | Valentini et al. | |
| 5,042,472 A | 8/1991 | Bunin | |
| 5,152,284 A | 10/1992 | Valentini et al. | |

(Continued)

FOREIGN PATENT DOCUMENTS

WO   WO 94/08552 A2   4/1994

(Continued)

OTHER PUBLICATIONS

Bisgaard, H. et al., Fine particle mass from the Diskus inhaler and Turbuhaler inhaler in children with asthma, European Respiratory Journal, 11: 1111-1115, May 1998.

(Continued)

*Primary Examiner*—Glenn K. Dawson
*Assistant Examiner*—Darwin P. Erezo
(74) *Attorney, Agent, or Firm*—Andrea G. Reister; Covington & Burling

(57) ABSTRACT

Inhaler and associated method for facilitating inhalation of dry powder medicaments by a patient. The inhaler is light and compact, allowing for convenient storage and portability by a patient. Additionally, a minimal number of steps are required by the patient to use the device from start to finish. The inhaler is self-contained, being provided to the patient with medicament having been pre-stored in a powder chamber. Upon release from this chamber, an accurate dosage of the dry powder medicament is available for inhalation. The inhaler may simply be disposed of following use.

32 Claims, 5 Drawing Sheets

U.S. PATENT DOCUMENTS

| | | |
|---|---|---|
| 5,239,991 A | 8/1993 | Chawla et al. |
| 5,239,992 A | 8/1993 | Bougamont et al. |
| 5,301,666 A | 4/1994 | Lerk et al. |
| 5,349,947 A | 9/1994 | Newhouse et al. |
| 5,437,271 A | 8/1995 | Hodson et al. |
| 5,507,281 A | 4/1996 | Kuhnel et al. |
| 5,524,613 A | 6/1996 | Haber et al. |
| 5,533,505 A | 7/1996 | Kallstrand et al. |
| 5,575,280 A | 11/1996 | Gupte et al. |
| 5,595,175 A | 1/1997 | Malcher et al. |
| 5,617,845 A | 4/1997 | Poss et al. |
| 5,647,349 A | 7/1997 | Ohki et al. |
| 5,651,359 A | 7/1997 | Bougamont et al. |
| 5,660,169 A * | 8/1997 | Kallstrand et al. ..... 128/203.15 |
| 5,673,686 A | 10/1997 | Villax et al. |
| 5,685,294 A | 11/1997 | Gupte et al. |
| 5,699,789 A | 12/1997 | Hendricks |
| 5,727,546 A | 3/1998 | Clarke et al. |
| 5,740,794 A | 4/1998 | Smith et al. |
| 5,785,049 A | 7/1998 | Smith et al. |
| 5,787,881 A | 8/1998 | Chawla |
| 5,797,391 A | 8/1998 | Cook et al. |
| 5,810,004 A | 9/1998 | Ohki et al. |
| 5,829,434 A * | 11/1998 | Ambrosio et al. ..... 128/203.15 |
| 5,860,419 A | 1/1999 | Davies et al. |
| 5,896,855 A | 4/1999 | Hobbs et al. |
| 5,918,594 A | 7/1999 | Asking et al. |
| 5,921,237 A | 7/1999 | Eisele et al. |
| 6,065,472 A | 5/2000 | Anderson et al. |
| 6,092,522 A | 7/2000 | Calvert et al. |
| 6,098,619 A | 8/2000 | Britto et al. |
| 6,102,035 A | 8/2000 | Asking et al. |
| 6,105,574 A | 8/2000 | Jahnsson |
| 6,116,237 A | 9/2000 | Schultz et al. |
| 6,116,238 A | 9/2000 | Jackson et al. |
| 6,119,853 A | 9/2000 | Garrill et al. |
| 6,142,145 A | 11/2000 | Dagsland et al. |
| 6,187,269 B1 | 2/2001 | Lancesseur et al. |
| 6,237,590 B1 | 5/2001 | Leedom et al. |
| 6,273,085 B1 | 8/2001 | Eisele et al. |
| 6,286,507 B1 | 9/2001 | Jahnsson |
| 6,332,461 B1 * | 12/2001 | Hyppola ................ 128/203.15 |
| 6,390,291 B1 * | 5/2002 | Garrill et al. ................ 206/204 |
| 6,575,160 B1 | 6/2003 | Volgyesi |
| 6,732,732 B1 | 5/2004 | Edwards et al. |
| 2003/0094173 A1 | 5/2003 | Burr et al. |

FOREIGN PATENT DOCUMENTS

| | | |
|---|---|---|
| WO | WO 00/64519 A1 | 11/2000 |
| WO | WO 01/07107 | 2/2001 |

OTHER PUBLICATIONS de Boer, A.H. et al., "Inhalation characteristics and their effects on in vitro drug delivery from dry powder inhalers, Part 1. Inhalation characteristics, work of breathing and volunteers' preference in dependence of the inhaler resistance," International Journal of Pharmaceutics 130: 231-244 (1996).

Dunbar, Craig A. et al., A Comparison of Dry Powder Inhaler Dose Delivery Characteristics Using a Power Criterion, PDA Journal of Pharmaceutical Science & Technology, 54(6): 4780484, Nov./Dec. 2000.

Feddah, Majid R. et al., In-Vitro Characterisation of Metered Dose Inhaler Versus Dry Powder Inhaler Glucocorticoid Products: Influence of Inspiratory Flow Rates, J. Pham. Pharmaceut. Sci. (www.ualberta.ca/-csps) 3(3): 317-324 (2000).

Koskela, T. et al., Efficacy of salbutamol via Easyhaler® unaffected by low inspiratory flow, Respiratory Medicine 94: 1229-1233 (Dec. 2000).

Nielsen, K.G. et al., Flow-dependent effect of formoterol dry-powder inhaled from the Aerolizer®, European Respiratory Journal, 10: 2105-2109 (Sep. 1997).

Richards, Robert and Saunders, Michael, Need for a comparative performance standard for dry powder inhalers, Thorax 48: 1186-1187 (Nov. 1993).

Ross, Danna L. and Schultz, Robert K., Effect of Inhalation Flow Rate on the Dosing Characteristics of Dry Powder Inhaler (DPI) and Metered Dose Inhaler (MDI) Products, Journal of Aerosol Medicine, 9: 215-226 (Nov. 2, 1996).

Smith, Karen J. et al., Influence of Flow Rate on Aerosole Particle Size Distributions from Pressurized and Breath-Actuated Inhalers, Journal of Aerosol Medicine, 11: 231-245 (Nov. 4, 1998).

* cited by examiner

INHALATION DEVICE AND METHOD

This application is a divisional of application Ser. No. 09/637,940 filed Aug. 14, 2000, now abandoned.

BACKGROUND OF THE INVENTION

1. Field of the Invention

The present invention relates generally to administration of medication. More specifically, the present invention relates to the administration of medication by a method and apparatus for facilitating inhalation of dry powder medicaments.

2. Related art

In the medical field, it is often desirable to administer various forms of medication to patients. Well known methods of introducing medication into the human body include the oral ingestion of capsules and tablets, intravenous injection through hypodermic needles, and numerous others. In one method, certain medications may be inhaled into a patient's respiratory tract and lungs through the nose or mouth. Certain of these medications, such as bronchodilators, corticosteroids, etc., for the treatment of asthma and other respiratory anomalies, may be aimed at the respiratory tract directly. Others are inhaled for purposes of systemic treatment, i.e. for treatment of any area of the body through absorption from the respiratory tract through the lung tissue, into the deep lungs, and into the bloodstream. Each of these medications comes in a variety of forms, including fluids, which are commonly administered as an aerosol vapor or mist, as well as solids. Inhalable solids typically take the form of fine, dry powders. Specialized devices, such as inhalers, are provided to assist the patient in directing these fine powder medications into the respiratory tract.

A variety of inhalers are known for the administration of dry powder medicaments. However, each of these inhalers suffers certain drawbacks. For example, U.S. Pat. No. 5,787,881 discloses an inhaler that is used with encapsulated dry powder medicaments. However, use of this device requires numerous steps and imposes a number of inconveniences on a user. For example, the medication capsules used with the device have an aperture formed therein prior to insertion into an opening in the inhaler. Therefore, there exists a danger that an amount of medication may be lost prior to or during insertion into the device. After insertion of the capsule, use of the device requires the additional step that a cover must be closed before the medication may be inhaled. Further inconveniences arise during periods of nonuse of the device. For example, because medication is not inserted into the device until just prior to use, the medication and the device may inadvertently become separated, and alone, each is useless. Furthermore, because the device is circular in shape, it is not as readily stored as a flatter device would be in locations such as wallet or pocket, for example.

The above inhaler and others which are known may be operated in a positive gas assisted manner, such as with a source of compressed air or other gas. These devices are inconvenient for a user in that the compressed gas source must be carried with the inhaler if medication is to be effectively administered. Also, these devices carry the additional danger that a pressurized container may become ruptured.

Propellant-free inhalers, which depend only on an inspiration by a user, are also known. One such device is disclosed in U.S. Pat. No. 5,575,280. This device houses in a storage chamber an amount of medication sufficient for administration of more than one dose. Just prior to each use, a notched wheel rotates to meter an amount of powder into a separate chamber for inhalation. However, if the medication does not properly fill such a notch, because of an air pocket, for example, an improper amount of medication may be administered following rotation of the wheel. This inaccuracy can potentially lead to ineffective treatment of an ailment, and thereby result in prolonged suffering by a patient.

Thus, there is a need in the art for an improved method and apparatus for inhalation of dry powder medicaments. What is needed is an inhaler having medication pre-stored therein, and which requires minimal steps by a user prior to use. Such a device would preferably come in a size and shape for portability and convenient storage by a user, and would be designed to avoid spillage or other events leading to inaccurate administration of medication, such that a proper dosage is administered each time such a device is used. The present invention, the description of which is fully set forth below, solves the need in the art for such improved methods and apparatus.

SUMMARY OF THE INVENTION

The present invention relates to a method and apparatus for facilitating inhalation of dry powder medicaments. In one aspect of the invention, an apparatus for inhaling powder is provided. The apparatus includes a casing that houses a powder chamber. The powder chamber is formed by a first wall that is coupled to the casing, and a second wall having a removable portion. At least one ventilation opening is defined in the casing to allow air to enter. The casing also includes a powder outlet opening to allow air and powder to exit from the casing.

In a further aspect of the present invention, another apparatus for inhaling powder is provided. The apparatus includes a casing having a first casing portion and a second casing portion. The casing portions are coupled such that they may slide with respect to each other. The casing contains a powder chamber, and has at least one ventilation opening to allow air to enter into the casing. The casing also includes a powder outlet opening. The powder chamber is configured such that sliding the first casing portion relative to the second casing portion causes the powder chamber to move from a closed position to an opened position. In the opened position, powder from the powder chamber can exit the device through the powder outlet opening.

In yet another aspect of the present invention, a method of dispensing powders by inhalation is provided. The method involves providing a powder inhalation device. The powder inhalation device includes a casing having a powder chamber that contains powder. A first wall that is coupled to the casing and a second wall having a removable portion define the powder chamber. At least one ventilation opening is defined in the casing to allow air to enter into the casing. The casing includes a powder outlet opening to allow powder to exit from the casing. The method further involves pulling a tether coupled to the removable portion of the second wall, thereby removing the removable portion and defining an opening in the second wall. A final aspect of the method involves inhaling the powder.

In still yet another aspect of the present invention, another method of dispensing powders by inhalation is provided. The method involves providing a powder inhalation device having a casing. The casing has a first casing portion and a second casing portion, with the casing portions being slidable with respect to each other. Defined in the casing is a powder chamber containing powder. The casing also includes a powder outlet opening and at least one ventilation opening to allow air to enter into the casing. The powder chamber is configured such that sliding the first casing portion relative to the second casing portion causes the powder chamber to move from a closed position to an opened position, allowing powder to exit the powder inhalation device through the powder outlet opening. The method further involves sliding the first casing portion relative to the second casing portion, thereby moving the powder chamber to the opened position. Finally, the method involves inhaling the powder.

Features and Advantages

One feature of the present invention is its compact and convenient size and shape. The dimensions of the inhaler render it ideal for storage in a pocket, or wallet or purse of a patient, with such items as identification or credit cards.

Another advantageous feature of the present invention is the accuracy of medicament dosage delivered thereby. Since only one dosage of medication is present in the inhaler during each use, the possibility of overdose is eliminated, and the medicament need not be metered prior to delivery. A patient may simply inhale all medicament present in the device.

The present invention also possesses the advantage that the medicament is stored inside the inhaler. The inhaler advantageously may be made from a material having a desiccant integral to it, or otherwise include a desiccant, to protect the medicament from moisture during storage. No capsules or other storage units need be carried other than the inhaler itself. In addition, the medicament is sealed securely inside the inhaler until only a moment prior to use, and thus the chances of spillage are greatly reduced.

Because the present invention operates only under the inhalative power of the patient, the inhaler carries the additional advantage that no accessory device, such as a compressed air cylinder or other propellant, needs to be used in conjunction with the present invention.

Another advantage of the present invention is that the medicament has been stored in a sealed, dry environment until just prior to administration. In addition, during inhalation, the medicament is subjected to mixing by a plurality of baffles contained in the device. These features help to ensure that the medicament exiting the inhaler and entering the patient's respiratory system is in the form of a fine dry powder, facilitating medicament deposition in the lungs. In addition, inhalation of finer powders is typically more comfortable for the patient.

Yet another advantage of the apparatus of the present invention is that it is disposable. A patient can simply use the inhaler, and dispose of it. Other steps such as cleaning, refilling and permanently storing are unnecessary.

BRIEF DESCRIPTION OF THE FIGURES

The present invention is described with reference to the accompanying drawings. In the drawings, like reference numbers indicate identical or functionally similar elements.

DETAILED DESCRIPTION OF THE PREFERRED EMBODIMENTS

Overview

The present invention provides an improved method and apparatus for dispensing dry powder medicaments for inhalation by a patient. As will be described in more detail below, an apparatus of the present invention is an inhaler having a compact and convenient shape. This inhaler contains a single dose of dry powder medicament, and may be disposed of following use by a patient. The inhaler includes features for allowing air to pass into and through the device as a patient inhales. In proper use, air will exit the inhaler carrying a full dose of medicament in the form of a fine, dry powder, with little risk of spillage. Following use, the inhaler may be disposed of.

The methods of the present invention use an inhaler to administer a single dose of dry powder medicament. As will be discussed in greater detail below, a user utilizes the method of the present invention by removing the inhaler from any protective wrapping. The fine powder medicament contained therein is released from a powder chamber and inhaled. The inhaler may then be disposed of.

Inhaler and Associated Method of the Present Invention

Figure 1:
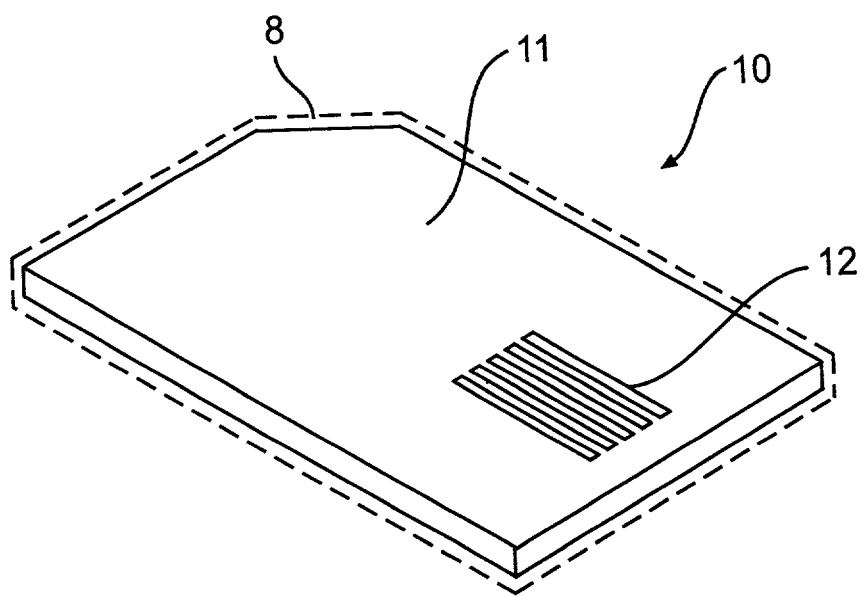
FIG. 1 is a perspective view of an embodiment of an inhalation device in accordance with the present invention.

An exemplary embodiment of the present invention will now be described. Referring to FIG. 1, an inhaler 10 of the present invention is shown. As is illustrated, the inhaler 10 is of a relatively thin, rectangular design. Preferably, the inhaler 10 is comparable in length and width to a standard credit card, and is the approximate thickness of two to three credit cards. Of course, the precise dimensions may vary in size and/or shape with a particular medication and dosage to be administered, or merely with preference. For example, a device being approximately 85 millimeters (mm) in length, 55 mm in width, and 3 mm thick has been contemplated. Because of the compact size and shape of the inhaler 10, the patient may readily carry the inhaler 10 in a pocket, or store it in a wallet or purse, such as with credit cards, identification cards, or similarly shaped items.

Figure 2:
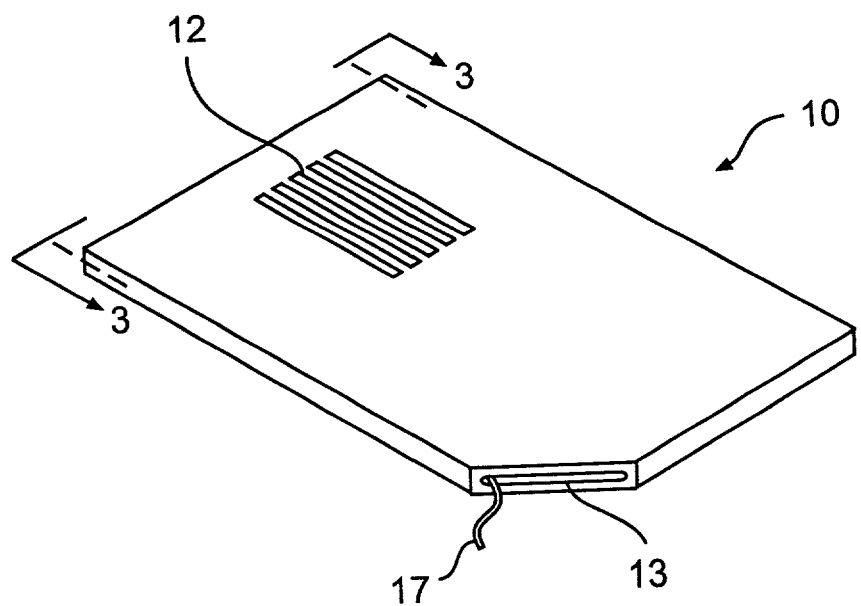
FIG. 2 is another perspective view of an embodiment of an inhalation device in accordance with the present invention.

As further illustrated in FIGS. 1 and 2, the inhaler 10 includes a casing 11 having a powder outlet opening 13 defined therein, through which a user of the inhaler 10 inhales a powder medicament to be dispensed. Prior to a time of use, the inhaler 10 may be contained in a sealed protective enclosure, such as a plastic package or wrapper 8, as seen in FIG. 1. The inhaler 10 further includes at least one ventilation opening 12 or air inlet defined in the casing 11 to allow a stream of ambient air to enter as the user draws air from the inhaler 10 through the powder outlet opening 13. One or more additional ventilation openings (see FIG. 3b) may be formed in the casing 11 in any desired position to allow one or more secondary or additional streams of air to enter the inhaler 10. Alternatively, secondary or additional air streams may be formed from a single air inlet by passageways internal to the inhaler 10. A leash or other similar structure, such as a tether 17, can be seen protruding from the powder outlet opening 13, as is illustrated in FIG. 2.

Figure 3A:
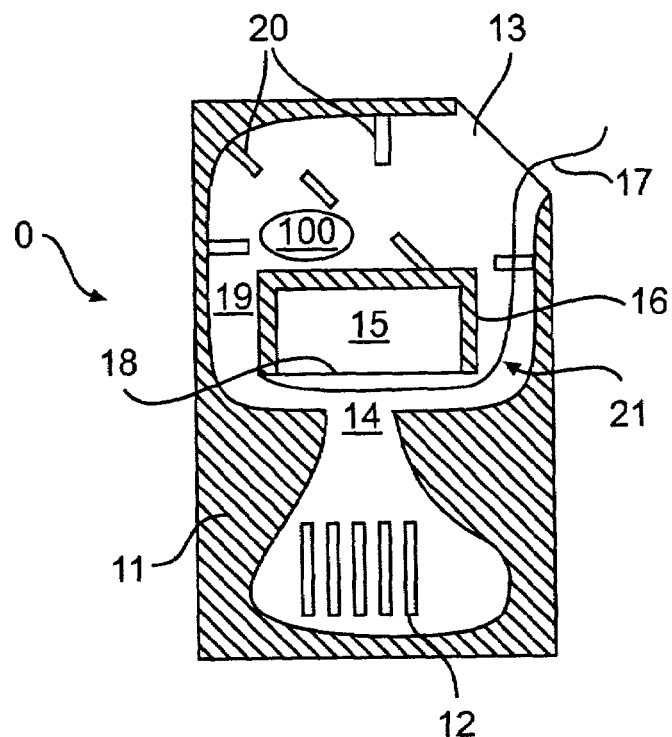
FIG. 3a is a cross sectional view along line 3—3 of FIG. 2 showing an internal arrangement of an inhalation device of the present invention.

Referring next to FIG. 3a, an embodiment of an internal structure is revealed for the inhaler 10. As discussed above with regard to external features, the inhaler 10 of FIG. 3a includes a casing 11 that has formed therein at least one ventilation opening 12 and a powder outlet opening 13. In addition, the casing 11 includes a powder chamber 15 defined by a first wall 16 coupled to the casing 11, and a second wall 18 having a removable portion. The second wall 18 is preferably formed at least partially by the tether 17, which protrudes from the powder outlet opening 13. Alternatively, the tether 17 may merely be connected to, rather than itself a part of, the removable portion. The casing 11 has defined therein exit channels 19 and 21, and a nozzle 14 integrally formed in the casing 11 and in fluid communication between at least one ventilation opening 12 and the powder outlet opening 13. A plurality of baffles 20 are disposed within the exit channels 19 and 21, as well as in the open space between the exit channels 19 and 21 and the powder outlet opening 13. At a time of manufacture, the casing 11 is preferably formed by two opposing portions that are to be attached together, with each of the above-described features formed as desired in one or the other of the opposing portions prior to their attachment. Alternatively, the inhaler 10 may be formed as a unitary device.

Figure 3B:
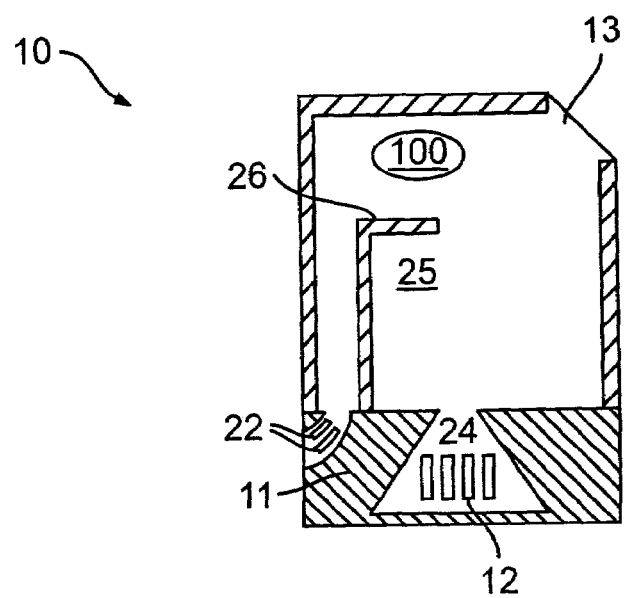
FIG. 3b is a cross sectional view along line 3—3 of FIG. 2 showing an alternative internal arrangement of an inhalation device of the present invention.

With reference to FIG. 3b, an alternative embodiment of an internal structure of the inhaler 10 is illustrated. Like the embodiment of FIG. 3a, this embodiment includes a casing 11 having at least one ventilation opening 12 and a powder outlet opening 13 defined therein. A nozzle 24 is integrally formed in the casing 11 and is in fluid communication between the at least one ventilation opening 12 and the powder outlet opening 13. In this embodiment, the inhaler 10 includes an alternative powder chamber 25 defined by a first wall 26 coupled to the casing 11. Prior to use, the powder chamber 25 will preferably be further defined by a second wall (not shown) having a removable portion, such as a tether or other removable portion connected thereto, as discussed above. The inhaler 10 may further be provided with one or more baffles, as in the embodiment of FIG. 3a. The inhaler 10 may also be provided with one or more additional ventilation openings 22, such that a secondary stream of air enters the casing 11.

The operation of an inhaler of the present invention will now be described. For convenience, the inhaler 10 of FIGS. 1 and 2 and the internal features of FIGS. 3a and 3b will be referred to. However, the following description is also applicable to other embodiments of the present invention.

When provided to a user, such as a patient, the inhaler 10 will preferably appear substantially as shown in FIG. 2, and will have been provided with a proper dosage of medicament in powder chamber 15. As noted, the inhaler 10 is preferably provided to a patient in a sealed protective enclosure 8, such as a plastic package or wrapper. While not necessary, sealing the inhaler 10 in a protective wrapper may help to prevent moisture in the ambient air from reaching the dry powder medicament housed therein, reducing clumping and thereby facilitating inhalation when a dose is administered. A reusable carrying case may also be utilized with multiple inhalers over time as a patient transports multiple doses of medicament.

When a patient is prepared to administer a dose of medicament, the patient first removes an inhaler 10 from its carrying case and/or protective wrapper 8. The patient then preferably holds the inhaler 10 substantially parallel to the ground and gently tugs on the tether 17 protruding from the powder outlet opening 13. Referring again to FIG. 3a, pulling on the tether 17 serves to at least partially remove the second wall 18 of the powder chamber 15, and to release medicament stored in the powder chamber 15 from its previously sealed condition. Preferably, the tether 17 and the associated portion of the second wall 18 are completely removed from the inhaler 10 by the patient prior to inhalation.

The inhaler 10 is now ready for use in administering a dosage of medicament. The patient's lips are used to form an airtight seal about the powder outlet opening 13. At this time, a relatively forceful inhalation action by the patient will draw air into the casing 11 of the inhaler 10 through at least one ventilation opening 12. The incoming air is forced through the nozzle 14, causing the air to accelerate as the space through which the air is passing narrows, and aiming the air directly into the dosage of medicament previously sealed in the powder chamber 15. Preferably, the powder medicament used will consist of particles of a very fine and low-density nature. Such particles are highly susceptible to aerolization, i.e. they readily mix with ambient air. The stream of air through the nozzle 14 causes the fine particles of medicament to become airborne, and to begin passing through the exit channels 19 and 21 towards the powder outlet opening 13. As noted above, one or more additional ventilation openings may allow one or more secondary or additional streams of air to enter the inhaler 10. These additional streams act to further mix with the powder medicament to facilitate aerolization of the medicament particles. As the airborne medicament passes through the exit channels 19 and 21 and the space about the powder outlet opening 13, the plurality of baffles 20 acts to break up any remaining clumps of medicament. Breaking up the medicament disperses the particles thereof to a size appropriate for effective respiration into the patient's respiratory tract, and makes inhalation more comfortable for the patient.

Preferably, a full dose of medicament will be administered by a single inhalation action by a patient. However, depending on a size of the dose, a patient's lung capacity generally, and a particular inhalation specifically, further inhalations may be necessary. The inhaler 10, including, for example, casing 11, may be in part or completely formed of a translucent or transparent material, revealing to a user whether a full dosage of medicament has been properly administered. Alternatively, a patient may have to learn through experience how to best self-administer a full dosage. Preferably, inhaler 10 is then properly disposed of. In such a disposable embodiment of the present invention, inhaler 10, including, for example, casing 11, is formed from a biodegradable material. One such biodegradable material is biodegradable plastic. Other suitable biodegradable materials would be apparent to one skilled in the art. Alternatively, reusable inhalers may be used in connection with individually provided medicament packets that would be placed in the powder chamber 15 prior to use. Such medicament packets, for use in reusable and disposable inhalers alike, may be prepared for use in any of a variety of ways. For example, a tether or similar arrangement, as discussed above, may be pulled by a user to release medicament stored in the packet. Alternatively, blister packs may be used. In another embodiment, the inhaler may be adapted with a blade or other puncturing or cutting device that may be manipulated by a patient to open a medicament packet. Further variations will be apparent to one skilled in the art.

In one embodiment of the present invention, inhaler 10, including, for example, casing 11, is formed from a material having a desiccant integral to it to protect against moisture during storage. One such material is, for example, a desiccant plastic. In an alternate embodiment of the present invention, a desiccant 100, as shown in FIGS. 3a, 3b, 6, and 7, is disposed in casing 11 to protect against moisture. It should be understood by one skilled in the art that the materials discussed herein for inhaler 10 are applicable to all embodiments of the invention.

Figure 4:
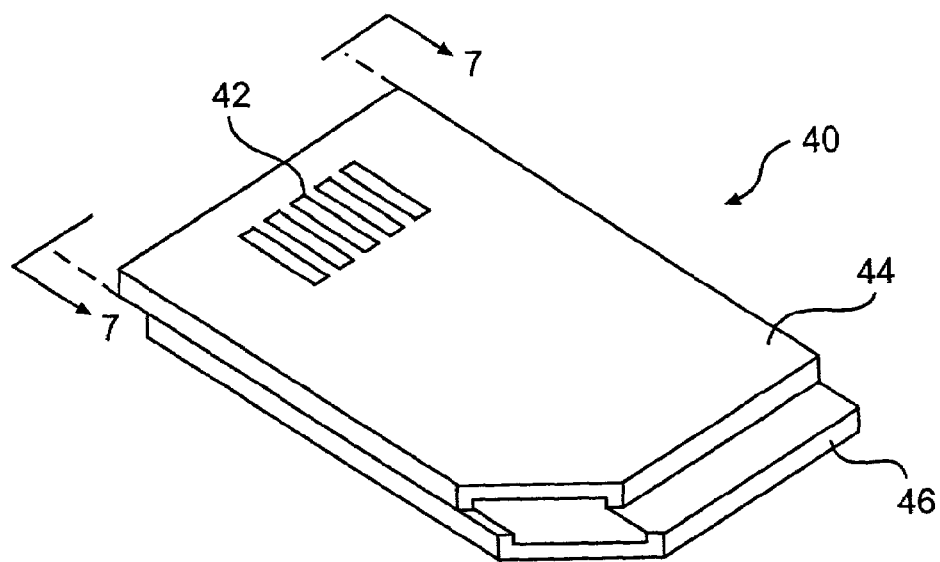
FIG. 4 is another embodiment of an inhalation device in accordance with the present invention, illustrated in a preferred opened position.
Figure 5:
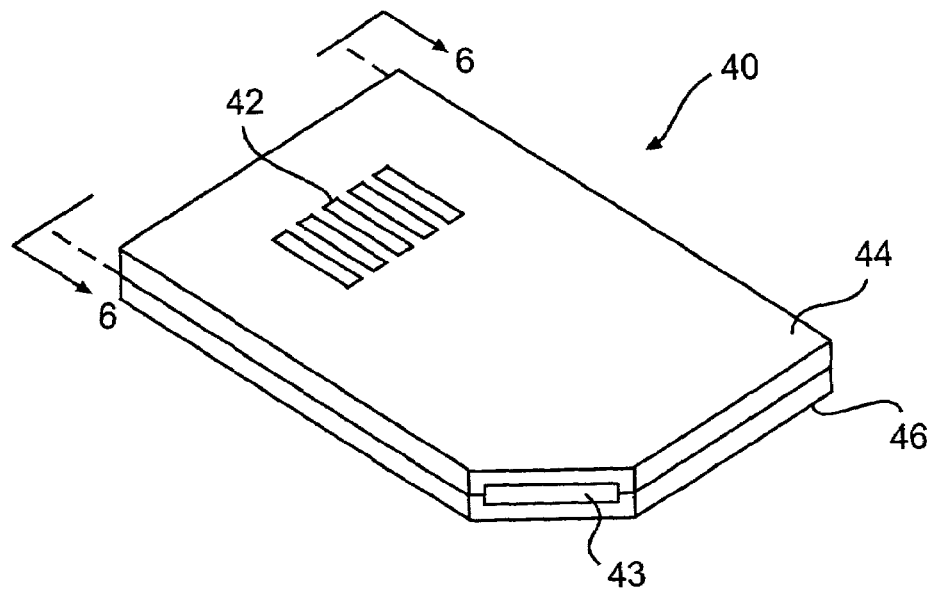
FIG. 5 is another embodiment of an inhalation device in accordance with the present invention, illustrated in a preferred closed position.
Figure 6:
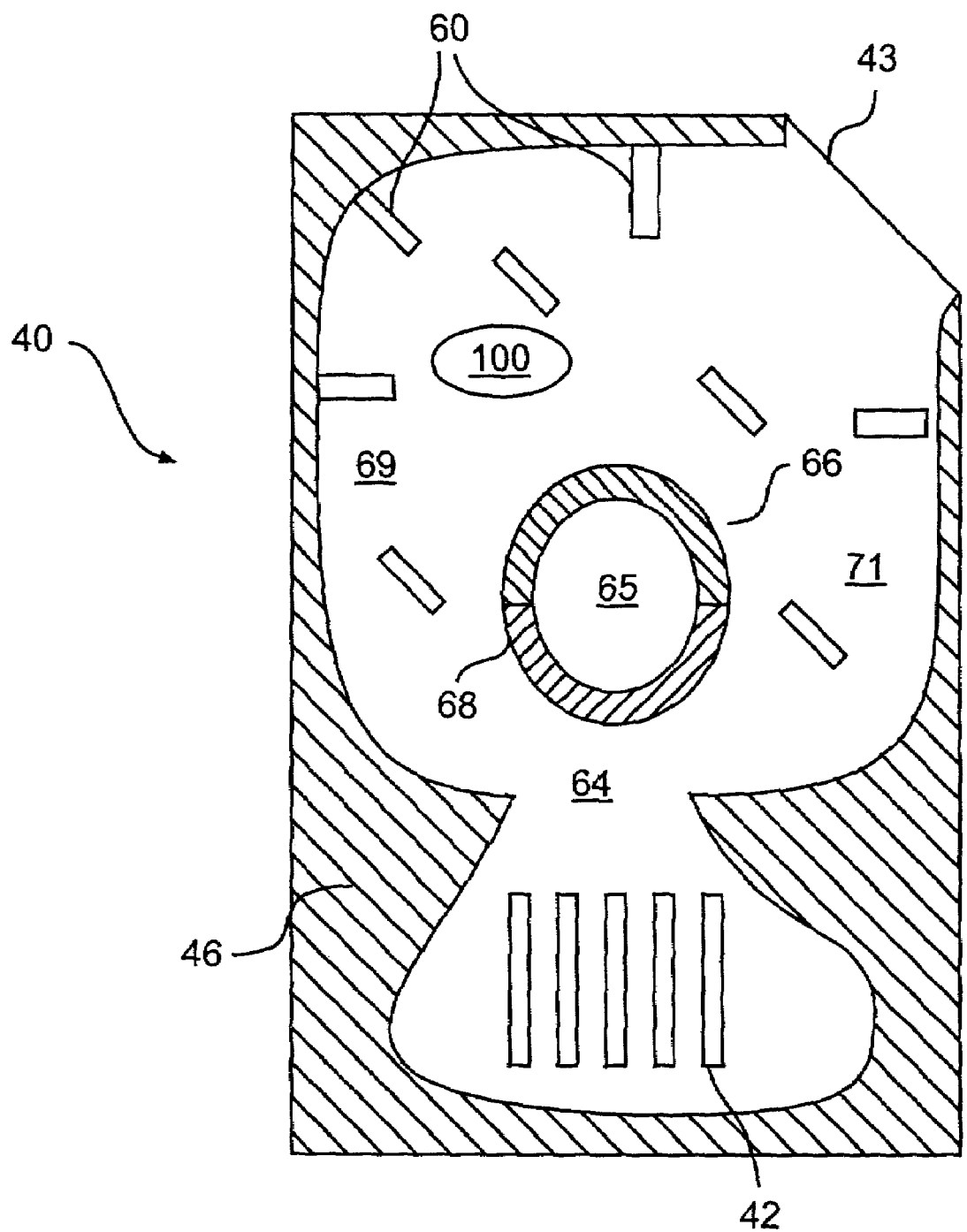
FIG. 6 is a cross sectional view of another embodiment of an inhalation device along line 6—6 of FIG. 5.

Referring to FIGS. 4–7, an embodiment of the present invention is illustrated which does not rely on a leash or tether to release medicament from a powder chamber prior to use. With reference to FIGS. 4 and 5, the casing of this inhaler 40 is formed of a first casing portion 44, and a second casing portion 46 slidably coupled to the first casing portion 44. Referring to FIG. 6, a second wall 68 of a powder chamber 65 is formed not from a portion of a tether as in the embodiments of FIGS. 3a and 3b, but from a material similar to that forming a first wall 66 of the powder chamber 65. The second wall 68 is coupled to a different casing portion than is the first wall 66, such that when the first casing portion 44 moves with respect to the second casing portion 46, the first wall 66 moves with respect to the second wall 68. Other features of this embodiment, including at least one ventilation opening 42, a powder outlet opening 43, a plurality of baffles 60, a nozzle 64 and exit channels 69 and 71, are substantially similar to and function in substantially the same manner as their analogous features described above with respect to FIGS. 1, 2, 3a and 3b.

When an inhaler 40 is provided to a patient, it will be in a closed position. As discussed above, the inhaler 40 will preferably be contained in a sealed protective enclosure (not shown), such as a plastic package or wrapper. Preferably, FIG. 4 illustrates the opened position while FIG. 5 shows the closed position. This arrangement leaves the inhaler 40 in its most compact position while it is not in use. Alternatively, FIG. 4 may illustrate the closed position and FIG. 5 the opened position. Such an arrangement would facilitate formation of an airtight seal about the powder outlet opening 43 by the patient, since the regions of the first casing portion 44 and the second casing portion 46 that form the powder outlet opening 43 will be in closer proximity to each other in this position.

Figure 7:
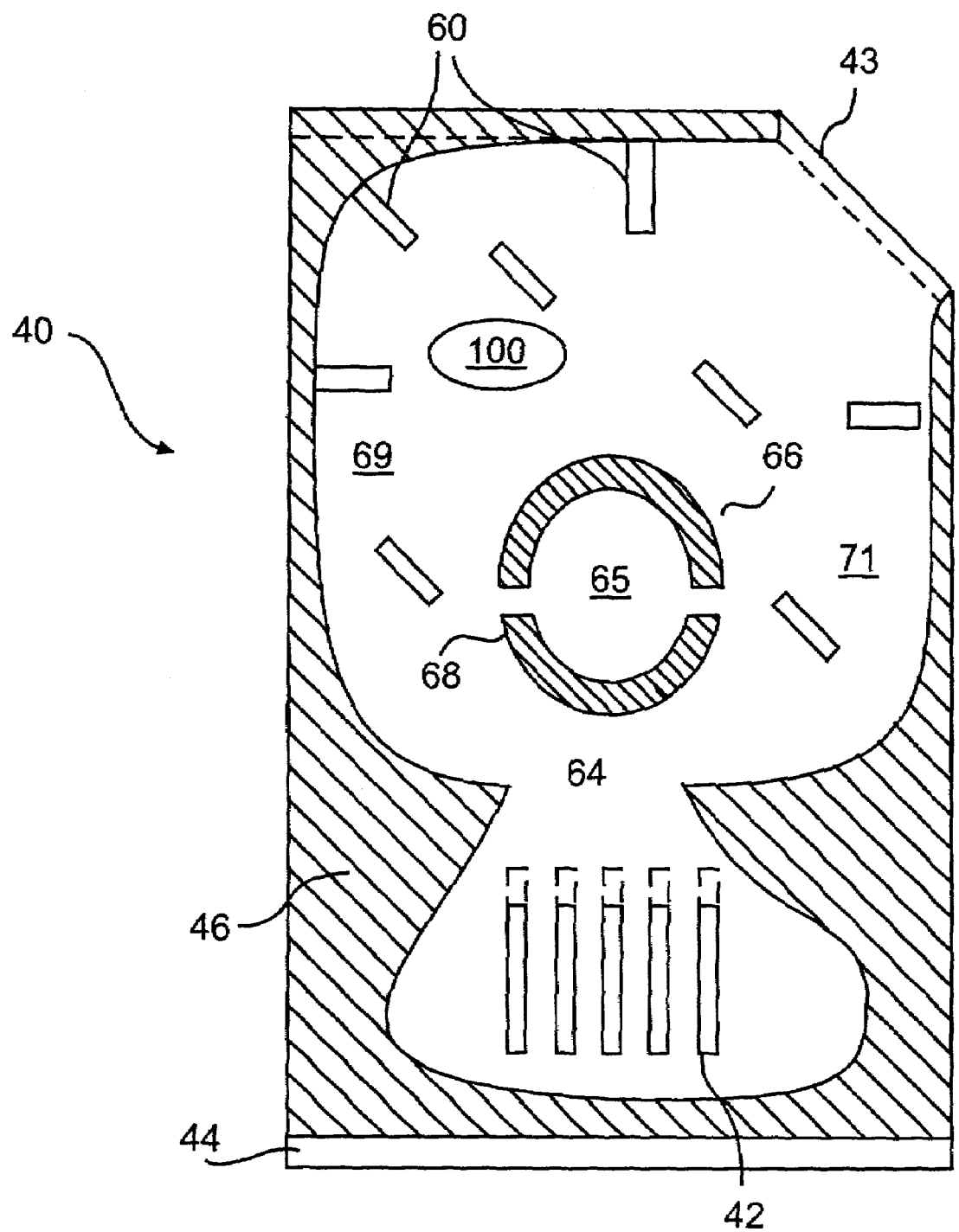
FIG. 7 is a cross sectional view of another embodiment of an inhalation device along line 7—7 of FIG. 4.

Referring now to FIG. 6, an internal arrangement of the inhaler 40 in the closed position may be seen. With the inhaler 40 in the closed position, the second wall 68 is disposed against the first wall 66 to define powder chamber 65. With this arrangement, when the inhaler 40 is in the closed position, the powder chamber 65 will likewise be in the closed position. Again, medicament to be administered will be housed within the powder chamber 65. FIG. 7 illustrates the internal arrangement of the inhaler 40 in the opened position. When the first casing portion 44 is moved with respect to the second casing portion 46 from the closed position to the opened position, the first wall 66 and second wall 68 of the powder chamber 65 separate, releasing the dry powder stored in the powder chamber 65. While the movable portion of the powder chamber 65 is here illustrated as a movable second wall 68, it should be noted that any movable portion may be used. For example, a relatively small plug may be removable from the top, bottom or sides of the powder chamber 65 upon movement of the first casing portion 44 with respect to the second casing portion 46. Additionally, the inhaler 40 may optionally be further designed such that the one or more ventilation openings 42 are open to outside air only when the inhaler 40 is in the opened position.

In the present embodiment, the closed position of the powder chamber 65 is preferably maintained merely by the pressure of the second wall 68 against the first wall 66, so long as the pressure is sufficient to prevent premature escape of the medicament housed within the powder chamber 65. The pressure results from a friction fit between the first casing portion 44 and the second casing portion 46, to which the second wall 68 and the first wall 66 are separately attached. Note that first wall 66 and the second wall 68 may each be attached to either the first casing portion 44 or the second casing portion 46, so long as the first wall 66 and the second wall 68 are attached to portions that are movable with respect to one another. Additional pressure between the first wall 66 and the second wall 68 of the powder chamber 65 may be induced if desired by in any way increasing the friction between the first casing portion 44 and the second casing portion 46, such as through the use of one or more detent portions. Alternatively, the junction between the first wall 66 and the second wall 68 may be provided with a releasable seal. This may be preferred where hermetic sealing of a medicament is a priority. However, such measures will typically be unnecessary since, as noted above, the inhaler 40 is preferably contained in a sealed protective enclosure when it is provided to the patient.

The operation of the inhaler 40 of this embodiment of the present invention will now be described. When a patient is prepared to administer a dose of medicament, the patient first removes the inhaler 40 from its protective wrapper. This arrangement allows a patient to slide the first casing portion 44 relative to the second casing portion 46 to cause the inhaler 40, and therefore the powder chamber 65 contained therein to move from a closed position to an opened position. This is analogous in a sense to the act of tugging the exposed tether 17 as was described with reference to FIG. 2, as it is this step that opens the powder chamber 65. Opening the inhaler 40 releases the medicament originally stored in the powder chamber 65. Because of the fine and low-density nature of the medicament preferably used in the inhaler 40, any reasonably forceful movement of air through the inhaler 40 will lead to aerolization of the powder released from the powder chamber 65 when the inhaler 40 is opened. The proper dosage of medicament may now be administered in accordance with the procedure described above with regard to the embodiments of FIGS. 1, 2, 3a and 3b.

CONCLUSION

While various embodiments of the present invention have been described above, it should be understood that they have been presented by way of example only, and not limitation. For example, the present invention is not limited to the physical arrangements or dimensions illustrated or described. Nor is the present invention limited to any particular design or materials of construction. As such, the breadth and scope of the present invention should not be limited to any of the above-described exemplary embodiments, but should be defined only in accordance with the following claims and their equivalents.

What is claimed is:

1. A powder inhalation device, comprising:
    a casing consisting of a first casing portion and a second casing portion, said first casing portion comprising a substantially planar first face portion and said second casing portion comprising a substantially planar second face portion, wherein said second casing portion is slidably coupled to said first casing portion;
a powder chamber disposed in said casing defined by a first wall coupled to said first face portion and a second wall coupled to said second face portion so that when said first casing portion moves with respect to said second casing portion, said first wall moves with respect to said second wall;
at least one ventilation opening defined in said casing to allow air to enter into said casing; and
a powder outlet opening, through which powder exits from said casing and around which a user's lips are used to form a seal, defined by said first casing portion and said second casing portion.

2. The powder inhalation device of claim 1, further comprising a nozzle integrally formed in said casing in fluid communication with said at least one ventilation opening.

3. The powder inhalation device of claim 2, wherein said powder chamber is disposed adjacent said nozzle, such that said nozzle converges toward said powder chamber and is configured to direct a stream of air into said powder chamber.

4. The powder inhalation device of claim 3, further comprising:
at least one secondary opening defined in said casing, wherein a secondary stream of air enters said casing through said secondary opening.

5. The powder inhalation device of claim 1, further comprising an exit channel defined by said casing, said exit channel being in fluid communication with said powder outlet opening.

6. The powder inhalation device of claim 5, further comprising a plurality of baffles disposed within said exit channel.

7. The powder inhalation device of claim 1, further comprising powder disposed within said powder chamber.

8. The powder inhalation device of claim 7, further comprising a wrapper encapsulating said casing.

9. The powder inhalation device of claim 1, wherein said device is dimensioned to form a compact configuration.

10. The powder inhalation device of claim 1, wherein said powder chamber is configured such that sliding said first casing portion relative to said second casing portion causes said powder chamber to move from a closed position to an open position, thereby allowing powder to exit the device through said powder outlet opening.

11. The powder inhalation device of claim 1, wherein at least a portion of said casing is formed from a translucent material.

12. The powder inhalation device of claim 1, wherein at least a portion of said casing is formed from a transparent material.

13. The powder inhalation device of claim 1, wherein said device is disposable.

14. The powder inhalation device of claim 1, wherein said casing is formed from a biodegradable material.

15. The powder inhalation device of claim 1, wherein said casing is formed from a material having an integral desiccant.

16. The powder inhalation device of claim 1, further comprising:
a desiccant disposed in said casing.

17. A powder inhalation device, comprising:
a casing, said casing consisting of a first casing portion and a second casing portion, said first casing portion comprising a substantially planar first face portion and said second casing portion comprising a substantially planar second face portion, wherein said second casing portion is slidably coupled to said first casing portion;
a powder chamber disposed in said casing;
at least one ventilation opening defined in said casing to allow air to enter into said casing;
a powder outlet opening, through which powder exits from said casing and around which a user's lips are used to form a seal, defined by said first casing portion and said second casing portion, wherein said powder chamber is configured such that said first and said second casing portions together enclose said powder chamber and sliding said first casing portion relative to said second casing portion causes said powder chamber to move from a closed position to an opened position, thereby allowing powder to exit the device through said powder outlet opening.

18. The powder inhalation device of claim 17, further comprising:
a nozzle integrally formed in said casing opposite said powder outlet opening and in fluid communication with said at least one ventilation opening, said nozzle converging toward said powder chamber and configured to direct a stream of air into said powder chamber.

19. The powder inhalation device of claim 18, further comprising:
an exit channel defined by said casing, said exit channel being in fluid communication with said powder outlet opening.

20. The powder inhalation device of claim 19, further comprising a plurality of baffles disposed within said exit channel.

21. The powder inhalation device of claim 18, further comprising:
at least one secondary opening defined in said casing, wherein a secondary stream of air enters said casing through said secondary opening.

22. The powder inhalation device of claim 17, further comprising powder disposed within said powder chamber.

23. The powder inhalation device of claim 22, further comprising a wrapper encapsulating said casing.

24. The powder inhalation device of claim 17, wherein at least a portion of said casing is formed from a translucent material.

25. The powder inhalation device of claim 17, wherein at least a portion of said casing is formed from a transparent material.

26. The powder inhalation device of claim 17, wherein said casing is formed from a biodegradable material.

27. The powder inhalation device of claim 17, wherein said casing is formed from a material having an integral desiccant.

28. The powder inhalation device of claim 17, further comprising:
a desiccant disposed in said casing.

29. A method for dispensing powder by inhalation, comprising:
sliding a first casing portion, comprising a substantially planar first face portion, relative to a second casing portion, comprising a substantially planar second face portion, of a powder inhalation device, thereby moving a powder chamber to an open position, wherein a casing for the powder inhalation device consists of the second casing portion slidably coupled to the first casing portion,
the powder chamber is defined by a first wall coupled to the first face portion and a second wall coupled to the second face portion so that when the first casing portion moves with respect to the second casing portion, the first wall moves with respect to the second wall, and the powder inhalation device comprises at least one ventilation opening defined in said casing to allow air to enter into the device, and a powder outlet opening, through which powder exits from said casing and around which a user's lips are used to form a seal, the powder outlet being defined by the first casing portion and the second casing portion; and inhaling powder from the device through said powder outlet opening.

30. The method of claim 29, further comprising:

removing a protective wrapper from said device.

31. The method of claim 29, further comprising:

providing the powder to the powder chamber.

32. The method of claim 31, wherein said providing includes inserting a powder packet into the powder chamber.

* * * * *